United States Patent
Doering et al.

(10) Patent No.: US 10,076,477 B2
(45) Date of Patent: Sep. 18, 2018

(54) AEROSOL COMPOSITIONS HAVING IMPROVED ACTIVE INGREDIENT APPLICATION

(71) Applicant: Henkel AG & Co. KGaA, Duesseldorf (DE)

(72) Inventors: Thomas Doering, Dormagen (DE); Gertraud Teckenbrock, Sprockhoevel (DE); Susanne Groehn, Dusseldorf (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/474,897

(22) Filed: Mar. 30, 2017

(65) Prior Publication Data
US 2017/0290751 A1 Oct. 12, 2017

(30) Foreign Application Priority Data
Apr. 6, 2016 (DE) ........................ 10 2016 205 699

(51) Int. Cl.
| | |
|---|---|
| *A61K 8/37* | (2006.01) |
| *A61Q 15/00* | (2006.01) |
| *A61K 8/26* | (2006.01) |
| *A61K 8/96* | (2006.01) |
| *A61K 8/49* | (2006.01) |
| *A61K 8/891* | (2006.01) |

(52) U.S. Cl.
CPC ............... *A61K 8/26* (2013.01); *A61K 8/37* (2013.01); *A61K 8/4973* (2013.01); *A61K 8/891* (2013.01); *A61K 8/965* (2013.01); *A61Q 15/00* (2013.01)

(58) Field of Classification Search
CPC .................................................... A61Q 15/00
See application file for complete search history.

(56) References Cited

U.S. PATENT DOCUMENTS

| | | | |
|---|---|---|---|
| 3,773,683 A | 11/1973 | Aubert | |
| 4,904,463 A | 2/1990 | Johnson | |
| 2015/0283048 A1* | 10/2015 | Banowski | ................ A61K 8/26 424/68 |

FOREIGN PATENT DOCUMENTS

| | | |
|---|---|---|
| DE | 19756454 C1 | 6/1999 |
| DE | 10333245 A1 | 7/2005 |
| DE | 102004011968 A1 | 9/2005 |
| EP | 0570085 A2 | 4/1993 |

* cited by examiner

*Primary Examiner* — Gina C Justice
(74) *Attorney, Agent, or Firm* — P. Scott Smith

(57) ABSTRACT

The present invention relates to aerosol compositions for body care, comprising:
a) at least one propellant, and
b) a composition A, which comprises
  (i) at least one perspiration-inhibiting antiperspirant active ingredient,
  (ii) at least one hydrophobized clay material, and
  (iii) propylene carbonate,
  wherein the weight ratio of the propylene carbonate (iii) to the hydrophobized clay material (ii) is 1.75:1.00 to 2.00:1.00.

The invention furthermore relates to the cosmetic use of a mixture of propylene carbonate (iii) and at least one hydrophobized clay material (ii) at a weight ratio of (iii):(ii) of 1.75:1.00 to 2.00:1.00 in antiperspirant aerosol compositions for improving the delivery rate of the antiperspirant active ingredient(s) when sprayed onto the skin, and to a cosmetic, non-therapeutic method for reducing or masking body odor in which an aerosol composition according to the invention is sprayed onto the skin.

20 Claims, No Drawings

AEROSOL COMPOSITIONS HAVING IMPROVED ACTIVE INGREDIENT APPLICATION

FIELD OF THE INVENTION

The present invention generally relates to propellant-containing aerosol compositions for body care, which, in addition to an antiperspirant active ingredient, comprise at least one hydrophobized clay material and propylene carbonate at a certain weight ratio.

BACKGROUND OF THE INVENTION

Washing, cleaning, and caring for the human body is an important basic need, and cosmetics manufacturers are always eager to satisfy the continuously changing and evolving needs of the consumers by providing new and/or improved products.

One fundamental component of daily hygiene is, for example, the effective elimination or at least the significant reduction of body odor and/or perspiration odor. These odors are created by the bacterial decomposition of various components of human (apocrine) perspiration on the skin, during which, among other things, low fatty acids (in particular $C_{4-10}$ fatty acids), ammonia, amines, indoles and sulfurous substances are created.

To combat body odor and/or perspiration odor, products are offered commercially in a wide variety of forms of application, such as powders, sticks, aerosol sprays, pump sprays, liquid and gel-like roll-ons, creams, gels, and saturated flexible substrates (known as deodorant wipes).

One variant of deodorant and antiperspirant compositions that is particularly preferred by many consumers is propellant-operated aerosol sprays.

These are characterized by convenient handling and dosability, hygienic use, and consistent effectiveness of the content sealed off from the outside atmosphere.

Commercially available aerosol dispensing devices always comprise an aerosol can and a spray head. They are pressurized and include propellant.

This system is necessary to ensure that the spraying properties are preserved over the entire usage duration of the aerosol spray. Otherwise, it would be possible for valves to clog, for example.

The disadvantage of antiperspirants of the aerosol type is that these often have a lower antiperspirant effectiveness compared to roll-ons or antiperspirant sticks.

The reason for this is that at times only approximately 20% of the required amount of antiperspirant active ingredients (usually astringent aluminum salts) from the aerosol compositions are delivered to the skin in a customary spray application.

Astringent aluminum salts are often present in antiperspirants in particulate form in a hydrophobic carrier (comprising at least one oil). The oil or oils of the hydrophobic carrier improve the adhesion of the suspended components to the skin, and moreover, serving as solvents, lubricants and spreading agents, help to uniformly distribute the antiperspirant agent on the skin.

Particulate active ingredients tend to precipitate from hydrophobic carriers, settle or agglomerate during storage. To prevent this, and to ensure stable suspension of the particulate active ingredients in antiperspirants over a long period of time, hydrophobically modified silicates, especially phyllosilicates such as montmorillonite, kaolinite, illite, beidellite, nontronite, saponite, hectorite, bentonite, smectite and/or talcum, are usually added to the carriers as suspending agents.

It was proposed in EP 570085 A2 to use propylene carbonate as an activator for hydrophobically modified clay materials in antiperspirants comprising a hydrophobic carrier.

The polar property of the propylene carbonate enables optimal dispersion of the hydrophobically modified phyllosilicates in anhydrous media. In this way, a viscosity is achieved, which is required for the stable suspension of particulate antiperspirant substances, and in particular of astringent aluminum salts, in the carrier oil.

The weight ratio of the propylene carbonate to the hydrophobically modified phyllosilicate is usually 1:3 (see also U.S. Pat. No. 3,773,683 and U.S. Pat. No. 4,904,463).

Despite the addition of propylene carbonate (at the above-mentioned weight ratio to the phyllosilicate), however, the above-mentioned delivery rate of antiperspirant active ingredients to the skin was not always satisfactory for conventional spray applications made of anhydrous aerosol antiperspirant compositions.

BRIEF SUMMARY OF THE INVENTION

An object of the present invention is to provide (anhydrous) aerosol compositions that do not exhibit or that minimize the above-described disadvantages.

In particular, propellant-containing aerosols were to be provided, which ensure an improved delivery rate of active ingredients (and in particular of antiperspirant active ingredients) to the application surface at a consistent spray volume.

A first subject matter of the present invention is thus an aerosol composition for body care, comprising a) at least one propellant, and b) a composition A, wherein composition A comprises (i) at least one perspiration-inhibiting antiperspirant active ingredient, (ii) at least one hydrophobized clay material, and (iii) propylene carbonate, wherein the weight ratio of the propylene carbonate (iii) to the hydrophobized clay material (ii) is 1.75:1.00 to 2.00:1.00.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Surprisingly, it was found that the delivery rate of suspended active ingredients from aerosol compositions comprising a hydrophobic carrier can be significantly improved if a mixture of hydrophobically modified phyllosilicates and propylene carbonate is added to the compositions at a certain weight ratio.

The active ingredient combination according to the invention is particularly suitable for the application from a hydrophobic, and preferably an anhydrous, carrier.

"Anhydrous" within the meaning of the present invention shall be understood to mean that composition A preferably comprises 0 to a maximum of 3 wt. %, more preferably 0 to a maximum of 2 wt. %, and in particular 0 to a maximum of 1 wt. % free water, wherein the quantity information is based on the weight of composition A.

The content of water of crystallization, hydration water, or similarly molecularly bound water that can be present in the components used, in particular in antiperspirant active ingredients (active ingredient combinations), does not constitute free water within the meaning of the present invention.

A first preferred embodiment of the invention is characterized in that composition A is anhydrous, which is to say comprises the active ingredient combination (i), (ii) and (iii) in an anhydrous carrier.

Suitable propellants within the meaning of the present invention can preferably be selected from propellants of the following group: propane, n-butane, isobutane, n-pentane, isopentane, dimethyl ether, carbon dioxide, nitrous oxide, fluorocarbons and/or chlorofluorocarbons. Particularly preferred propellants are propane, n-butane, isobutane, n-pentane, isopentane and/or the mixtures thereof, a mixture of propane and n-butane having a preferred weight ratio of propane/n-butane of 10 to 40/60 to 90, and particularly preferably of 10 to 20/80 to 90, being particularly preferred.

The propellant or propellants can preferably be present in the aerosol compositions according to the invention in amounts of 10 to 90 wt. %, more preferably 20 to 90 wt. %, particularly preferably 30 to 90 wt. %, and in particular 60 to 90 wt. %, wherein the quantities are based on the total aerosol composition.

In a further preferred embodiment, aerosol compositions according to the invention are characterized by comprising propane, n-butane, isobutane, n-pentane, isopentane and/or the mixtures thereof as propellant a).

Still another preferred embodiment of the invention is characterized in that,
propellant a) is present in a percentage by weight of 10 to 90 wt. % relative to the total weight of the aerosol composition, and
composition A is present in a percentage by weight of 10 to 40 wt. % relative to the total weight of the aerosol composition.

Suitable hydrophobized clay materials (ii) according to the invention shall preferably be understood to mean hydrophobized smectites, and preferably montmorrillonites, hectorites and/or bentonites.

What are known as bentones are particularly advantageous within the meaning of the present invention, which is to say organic derivatives of montmorrillonites (or bentonites) and/or hectorites that are hydrophobized by way of ion exchange reactions with cationic surfactants, preferably with alkylammonium bases, and in particular with mono- and/or di-$C_{10}$-$C_{24}$-alkyl-di-$C_1$-$C_4$-alkylammonium salts.

Stearalkonium hectorites are particularly preferred according to the invention, which is to say reaction products of hectorite and stearalkonium chlorides, such as the compounds known under the INCI names Disteardimonium Hectorite and/or Quaternium-18 Hectorite. These are available under the trade names Bentone® 27 and Bentone® 38 from Nordmann & Rassmann, for example.

Stearalkonium bentonites are likewise preferred according to the invention, such as Quaternium-90 Bentonite and/or Quaternium-18 Bentonite, which are available from Süd-Chemie and Rockwood under the trade name Tixogel®.

The at least one hydrophobized clay material (ii) is preferably used in the aerosol compositions according to the invention in amounts of 0.5 to 3.5 wt. %, preferably 0.5 to 3.0 wt. %, particularly preferably 1.0 to 3.0 wt. %, and in particular 1.5 to 2.5 wt. %, wherein the quantity information is based on the weight of compositions A.

In a second preferred embodiment, aerosol compositions according to the invention comprise montmorrillonites, hectorites and/or bentonites, which were hydrophobically modified with cationic surfactants, preferably with mono- and/or di-$C_{10}$-$C_{24}$-alkyl-di-$C_1$-$C_4$-alkylammonium salts, as hydrophobized clay material (ii).

Within the present embodiment, it is particularly preferred if the hydrophobized clay material (ii) is selected from distearyldimethylammonium hectorite (INCI: Disteardimonium Hectorite) and/or from the compounds known under the INCI names Quaternium-18 Hectorite, Stearalkonium Bentonite and/or Quaternium-18 Bentonite.

A third preferred embodiment of the invention is characterized in that the percentage by weight of the at least one hydrophobized clay material (ii), and preferably of the distearyldimethylammonium hectorite and/or a compound known under the INCI names Quaternium-18 Hectorite, Stearalkonium Bentonite and/or Quaternium-18 Bentonite, relative to the total weight of composition A is 0.5 to 3.5 wt. %, preferably 0.5 to 3.0 wt. %, particularly preferably 1.0 to 3.0 wt. %, and in particular 1.5 to 2.5 wt.

It was found that the delivery rate of antiperspirant active ingredients to the skin among compositions according to the invention (and thus the antiperspirant effectiveness thereof) is the greatest when propylene carbonate is present at a narrowly defined weight ratio to the hydrophobized clay material.

The best results were able to be achieved when the weight ratio of propylene carbonate (iii) to the hydrophobized clay material (ii) is 1.75:1.00 to 2.00:1.00.

According to a fourth preferred embodiment, the percentage by weight of propylene carbonate (iii) relative to the total weight of composition A is 1.0 to 7.0 wt. %, more preferably 1.5 to 6.0 wt. %, particularly preferably 2.0 to 5.0, and in particular 2.5 to 4.0 wt. %.

Suitable perspiration-inhibiting antiperspirant active ingredients (i) according to the invention are preferably water-soluble astringent inorganic and/or organic salts of aluminum, zirconium and zinc, or arbitrary mixtures of these salts.

Particularly preferred antiperspirant active ingredients are selected from the aluminum chlorohydrates, such as aluminum sesquichlorohydrate, aluminum chlorohydrex propylene glycol (PG) or aluminum chlorohydrex polyethylene glycol (PEG), aluminum sesquichlorohydrex PG or PEG, aluminum PG dichlorohydrex or aluminum PEG dichlorohydrex, aluminum hydroxide, furthermore selected from the aluminum zirconium chlorohydrates, such as aluminum zirconium trichlorohydrate, aluminum zirconium tetrachlorohydrate, aluminum zirconium pentachlorohydrate, aluminum zirconium octachlorohydrate, the aluminum zirconium chlorohydrate glycine complexes such as aluminum zirconium trichlorohydrex glycine, aluminum zirconium tetrachlorohydrex glycine, aluminum zirconium pentachlorohydrex glycine, aluminum zirconium octachlorohydrex glycine, potassium aluminum sulfate ($KAl(SO_4)_2 \cdot 12\, H_2O$, Alaun), aluminum undecylenoyl collagen amino acid, sodium aluminum lactate+aluminum sulfate, sodium aluminum chlorohydroxy lactate, aluminum bromohydrate, aluminum chloride, the complexes of zinc and sodium salts, the complexes of lanthanum and cerium, the aluminum salts of lipoamino acids, aluminum sulfate, aluminum lactate, aluminum chlorohydroxy allantoinate, sodium aluminum chlorohydroxy lactate, zinc chloride, zinc sulfocarbolate, zinc sulfate, and zirconium chlorohydrate.

According to the invention, "water solubility" shall be understood to mean a solubility of at least 5 wt. % in water at 20° C., which is to say that amounts of at least 5 g of the antiperspirant active ingredient are soluble in 95 g water at 20° C. The antiperspirant active ingredients can be used in the form of aqueous solutions.

Particularly preferred aerosol compositions according to the invention are characterized by comprising at least one astringent aluminum salt, preferably aluminum chlorohydrate, aluminum sesquichlorohydrate and/or aluminum chloride, as the perspiration-inhibiting antiperspirant active ingredient in a total amount of 5 to 60 wt. %, preferably of 10 to 50 wt. %, and in particular 15 to 40 wt. %, wherein the quantity information is based on the total weight of composition A.

A fourth preferred embodiment of the invention is characterized in that the aerosol composition comprises at least one antiperspirant active ingredient (i), selected from astringent aluminum salts, and preferably from aluminum chlorohydrate, aluminum sesquichlorohydrate and/or aluminum chloride, in a percentage by weight relative to the total weight of composition A of 5 to 60 wt. %, preferably of 10 to 50 wt. %, and in particular of 15 to 40 wt. %.

As stated above, the active ingredient combination (i) to (iii) according to the invention is particularly well-suited for the application from a hydrophobic, and preferably an anhydrous, carrier.

For optimal sprayability of the aerosol compositions according to the invention, it is advantageous if composition A comprises an oil (which is not an essential oil, perfume oil and/or emulsifier) that is liquid under normal conditions as the hydrophobic carrier.

Particularly suited oils comprise at least 90 wt. % of oil components liquid at 20° C.

Suitable oils are preferably used in composition A in amounts of 30 to 85 wt. %, more preferably of 35 to 80 wt. %, particularly preferably of 40 to 75 wt. %, and particularly preferably of 45 to 70 wt. %, in each case based on the total weight of the anhydrous composition A.

Suitable oils can be selected from:
  volatile silicone oils, which may be cyclic, such as octamethylcyclotetrasiloxane, decamethylcyclopentasiloxane and dodecamethylcyclohexasiloxane, and mixtures thereof, as they are present in the commercial products DC 244, 245, 344 and 345 from Dow Corning, for example, or they may be linear, such as hexamethyldisiloxane ($L_2$), octamethyltrisiloxane ($L_3$), decamethyltetrasiloxane ($L_4$), arbitrary mixtures of two and three of $L_2$, $L_3$ and/or $L_4$, as they are present in the commercial products DC 2-1184, Dow Corning® 200 (0.65 cSt) and Dow Corning® 200 (1.5 cSt) from Dow Corning, for example;
  non-volatile higher molecular weight linear dimethylpolysiloxanes, commercially available under the designations Dow Corning® 190, Dow Corning® 200 Fluid, for example, having viscosities in the range of 5 to 100 cSt, preferably 5 to 50 cSt, or 5 to 10 cSt, and Baysilon® 350 M;
  the esters of linear or branched, saturated or unsaturated alcohols having 2 to 5 carbon atoms with linear or branched, saturated or unsaturated carboxylic acid having 10 to 30 carbon atoms, such as isopropyl myristate, isopropyl palmitate, isopropyl stearate, isopropyl isostearate, isopropyl oleate, n-butyl stearate, ethylene glycol dioleate and dipalmitate;
  the esters of at least one linear or branched, saturated or unsaturated alcohol having 4 to 30 carbon atoms and at least one linear or branched, saturated or unsaturated carboxylic acid having 8 to 30 carbon atoms, such as 2-ethylhexyl laurate, 2-ethylhexyl myristate, 2-ethylhexyl palmitate, 2-ethylhexyl cocoate, 2-ethylhexyl stearate, 2-ethylhexyl isostearate, hexyldecyl laurate, hexyldecyl stearate, isooctyl stearate, isononyl isononanoate, isononyl stearate, isotridecyl nonanoate, 2-octyldodecyl palmitate and/or isocetyl stearate;
  the esters of at least one $C_2$-$C_7$ monocarboxylic, dicarboxylic or tricarboxylic acid, which can optionally comprise one or more hydroxyl groups, and at least one linear or branched, saturated or unsaturated alcohol having 1 to 30 carbon atoms, such as methyl, ethyl, n-propyl, isopropyl, n-butyl, 2-butyl or the tert. butyl esters of glycolic acid, lactic acid, malic acid, tartaric acid, citric acid, oxalic acid, malonic acid, succinic acid, glutaric acid and/or adipic acid, and particularly preferably triethyl citrate;
  the benzoic acid esters of linear or branched $C_{8-22}$ alkanols, such as the commercial products Finsolv® TN ($C_{12}$-$C_{15}$ alkylbenzoate), Finsolv® SB (isostearyl benzoate) and Finsolv® EB (ethylhexyl benzoate);
  the addition products of ethylene oxide and/or propylene oxide to monohydric or polyhydric $C_{3-20}$ alkanols, such as butanol, butanediol, myristyl alcohol and stearyl alcohol, such as PPG-14 butyl ether (Ucon Fluid® AP), PPG-9 butyl ether (Breox® B25), PPG-10 butanediol (Macol® 57), PPG-3 myristyl ether (Witconol® APM) and PPG-15 stearyl ether (Arlamol® E);
  liquid paraffin oils, isoparaffin oils, such as the commercial products of the Permethyl® series, and in particular isododecane, isohexadecane and isoeicosane, and synthetic hydrocarbons, such as polyisobutene or polydecene, and alicyclic hydrocarbons, such as the commercial product 1,3-di-(2-ethylhexyl)-cyclohexane (Cetiol® S);
  the branched, saturated or unsaturated fatty alcohols having 6 to 30 carbon atoms. These alcohols are frequently also referred to as Guerbet alcohols since they can be obtained by way of the Guerbet reaction. Particularly preferred alcohol oils are hexyl decanol (Eutanol® G), octyl dodecanol and 2-ethylhexyl alcohol, for example;
  mixtures of Guerbet alcohols and Guerbet alcohol esters, such as the commercial product Cetiol® PGL (hexyldecanol and hexyldecyl laurate);
  the symmetric, asymmetric or cyclic esters of carbonic acid with fatty alcohols, such as glycerin carbonate, propylene carbonate, dicaprylyl carbonate (Cetiol® CC), or the esters from German unexamined application DE 19756454;
  triglycerides of linear or branched, saturated or unsaturated, optionally hydroxylated $C_{8-30}$ fatty acids. The use of natural oils can be particularly suitable, such as soy bean oil, cottonseed oil, sunflower oil, palm oil, palm kernel oil, linseed oil, almond oil, castor oil, corn oil, olive oil, rapeseed oil, sesame oil, safflower oil, wheat germ oil, peach kernel oil, and the liquid components of coconut oil, and the like. However, synthetic triglyceride oils are also suitable, in particular capric/caprylic triglycerides, such as the commercial products Myritol® 318 or Myritol® 331 (Cognis) or Miglycol® 812 (Hüls) comprising unbranched fatty acid esters and glyceryl triisostearin and the commercial products Estol® GTEH 3609 (Uniqema) or Myritol® GTEH (Cognis) comprising branched fatty acid esters;
  dicarboxylic acid esters of linear or branched $C_2$ to $C_{10}$ alkanols, in particular diisopropyl adipate, di-n-butyl adipate, di-(2-ethylhexyl) adipate, dioctyl adipate, diethyl-/di-n-butyl/dioctyl sebacate, diisopropyl sebacate, dioctyl malate, dioctyl maleate, dicaprylyl maleate, diisooctyl succinate, di-2-ethylhexyl succinate, and di-(2-hexyldecyl) succinate; and di-n-alkyl ethers having a total of 12 to 36, and in particular 12 to 24, carbon atoms, such as di-n-octylether (Cetiol® OE), di-n-n-hexyl-n-octylether and n-octyl-n-decylether.

Especially particularly preferred oils within the meaning of the present invention are volatile cyclic silicone oils, such as decamethylcyclopentasiloxane and dodecamethylcyclohexasiloxane, volatile linear silicone oils, such as hexamethyldisiloxane ($L_2$), octamethyltrisiloxane ($L_3$) and decamethyltetrasiloxane ($L_4$), and arbitrary mixtures of two and three of $L_2$, $L_3$ and/or $L_4$, volatile and non-volatile linear silicone oils from the series Dow Corning 200 Fluid having viscosities of 0.65; 1.0; 1.5 and 5 cSt, the ester oils isopropyl myristate, isopropyl palmitate and/or ethylhexyl palmitate, the benzoic acid esters of linear or branched $C_{8-22}$ alkanols, and in particular the commercial product Finsolv® TN ($C_{12}$-$C_{15}$ alkyl benzoate), $C_{12}$-$C_{15}$ alkyl lactate, di-$C_{12}$-$C_{13}$ alkyl malate, phenoxyethyl octanoate, PPG-14 butyl ether (Ucon Fluid® AP), furthermore carbonic acid esters, and in particular propylene carbonate, the addition products of ethylene oxide and/or propylene oxide to monohydric or polyhydric $C_{3-20}$ alkanols, such as butanol, butanediol, myristyl alcohol and stearyl alcohol, such as PPG-14 butyl ether, and esters of at least one $C_2$-$C_7$ mono-, di- or -tri-(hydroxy) carbonic acid with at least one linear or branched, saturated or unsaturated alcohol having 1 to 30 carbon atoms, and in particular triethyl citrate.

Particularly preferred oils are volatile cyclic silicone oils, such as decamethylcyclopentasiloxane, ester oils, such as isopropyl myri state, ethylhexyl palmitate and/or triethyl citrate, benzoic acid esters of linear or branched $C_{8-22}$ alkanols, and in particular the commercial product Finsolv® TN ($C_{12}$-$C_{15}$ alkyl benzoate), and addition products of ethylene oxide and/or propylene oxide to monohydric or polyhydric $C_{3-20}$ alkanols, and in particular PPG-14 butyl ether.

It may be preferred according to the invention to use mixtures of the aforementioned oils. In particular, mixtures of two oil component types, such as a volatile silicone oil and ester oil, are preferred. Oil mixtures comprising at least one volatile cyclic silicone oil are particularly preferred. Oil mixtures that predominantly, which is to say a fraction of more than 50 wt. % (based on the total oil mixture), comprise at least one volatile cyclic silicone oil, are exceptionally preferred. Furthermore, preferred are oil mixtures comprising 50 to 95 wt. %, and particularly preferably 60 to 90 wt. %, of at least one volatile cyclic silicone oil in combination with 1 to 30 wt. %, particularly preferably 2 to 20 wt. %, and in particular 3 to 10 wt. %, of at least one ester oil, in particular isopropyl myristate, ethylhexyl palmitate and/or triethyl citrate, wherein the quantity information is based on the total weight of composition A according to the invention.

Particularly preferred compositions A according to the invention comprise a mixture of at least two of the above-mentioned oils that are liquid under normal conditions, namely room temperature and pressure (25 C and 1 ATM) as the hydrophobic carrier, and more preferably a mixture of at least two, and particularly preferably of at least three, of the following oils: volatile cyclic silicone oils such as decamethylcyclopentasiloxane and/or dodecamethylcyclohexasiloxane, non-volatile silicone oils such as dimethicone, ester oils such as isopropyl myristate, ethylhexyl palmitate and/or isopropyl palmitate, esters such as triethyl citrate, 2-phenoxyethyl octanoate and/or alkoxylated ethers such as PPG-14 butyl ether.

A fifth preferred embodiment is characterized in that composition A comprises at least one oil that is liquid under normal conditions, and preferably at least one ester oil and/or at least one silicone oil, wherein the percentage by weight of the liquid oil relative to the total weight of composition A is preferably 30 to 85 wt. %, more preferably 35 to 80 wt. %, particularly preferably 40 to 75% by weight, and in particular 45 to 70 wt. %.

Within the present embodiment, it is particularly preferred if composition A comprises, as the liquid oil, a mixture of
   triethyl citrate in a percentage by weight of 0.1 to 10.0 wt. %, preferably of 0.3 to 5.0 wt. %, and in particular of 0.5 to 2.0 wt. % relative to the total weight of composition A;
   at least one volatile silicone oil in a percentage by weight of 20.0 to 70.0 wt. %, preferably of 25.0 to 60.0 wt. %, and in particular of 35.0 to 50.0 wt. % relative to the total weight of composition A; and
   at least one $C_{10}$-$C_{24}$ carboxylic acid ester, and preferably a branched $C_{10}$-$C_{24}$ carboxylic acid ester, in a percentage by weight of 2.0 to 20.0 wt. %, preferably of 3.0 to 18.0 wt. %, and in particular of 6.0 to 10.0 wt. % relative to the total weight of composition A.

In a further preferred embodiment, the aerosol compositions according to the invention can furthermore comprise at least one deodorizing active ingredient, which is selected from the group consisting of odor absorbers, deodorizingly acting ion exchangers, antimicrobial active ingredients, prebiotically active components, such as inhibitors of the enzymes responsible for the decomposition of sweat, or, particularly preferably, combinations of these active ingredients.

Silicates can serve as preferred odor absorbers, which advantageously also support the rheological properties of composition A according to the invention. The particularly preferred silicates include in particular phyllosilicates, and among these in particular montmorillonite, kaolinite, illite, beidellite, nontronite, saponite, hectorite, bentonite, smectite, and talcum. Further particularly preferred odor absorbers are, for example, zeolites, zinc ricinoleate, cyclodextrins, certain metal oxides, such as aluminum oxide, and chlorophyll.

Odor absorbers are preferably used in the aerosol preparations according to the invention in an amount of 0.1 to 10 wt. %, particularly preferably of 0.5 to 7 wt. %, and in particular preferably of 1 to 5 wt. %, in each case based on the total weight of composition A.

Preferred aerosol compositions according to the invention are characterized by furthermore comprising at least one odor absorber, and preferably a silicate, in composition A.

Antimicrobial active ingredients shall be understood to mean those active ingredients which reduce the number of odor-causing bacteria on the skin, or which inhibit the growth of the same. These bacteria include, among other things, various species from the group of the Staphylococci (such as *Staphylococcus hominis*), the group of the Corynebacteria (such as *Corynebacterium xerosis, Corynebacterium* CDCG2), Anaerococci (such as *Anaerococcus octavius*), and Micrococci.

The odorant mixtures Protectate HR and Protectate MOD 2 from Symrise can preferably be used as antimicrobial active ingredients.

The odorant mixture Protectate HR from Symrise comprises 25 to 50 wt. % phenoxyethanol, 5 to 10 wt. %

2-methyl-5-phenylpentan-1-ol bearing the trivial name Rosaphen, 34 to 70 wt. % 2-benzylheptan-1-ol bearing the trivial name Jasmol, 1 to 5 wt. % 4-methoxybenzyl alcohol (anise alcohol) and 0.01 to 1 wt. % 5-methyl-2-isopropylphenol (Thymol). The odorant mixture Protectate MOD 2 from Symrise comprises 25 to 45 wt. % phenoxyethanol, 5 to 10 wt. % 2-methyl-5-phenylpentan-1-ol and 45 to 70 wt. % 2-benzylheptan-1-ol.

Furthermore, organohalogen compounds and organohalides, quaternary ammonium compounds, a number of plant extracts and zinc compounds are preferred antimicrobial active ingredients. These include, among other things, triclosan, chlorhexidine and chlorhexidine gluconate, 3,4,4'-trichlorocarbanilide, bromochlorophene, dichlorophene, chlorothymol, chloroxylenol, hexachlorophene, dichloro-m-xylenol, dequalinium chloride, domiphen bromide, ammonium phenolsulfonate, benzalkonium halide, benzalkonium cetyl phosphate, benzalkonium saccharinate, benzethonium chloride, cetylpyridinium chloride, laurylpyridinium chloride, lauryl isoquinolinium bromide, methylbenzethonium chloride. Moreover, phenol, phenoxyethanol, disodium dihydroxyethylsulfosuccinylundecylenate, sodium bicarbonate, zinc lactate, sodium phenolsulfonate and zinc phenolsulfonate, ketoglutaric acid, terpene alcohols, such as the particularly preferred farnesol, chlorophyllin-copper complexes, α-monoalkylglycerol ethers comprising a branched or linear, saturated or unsaturated, optionally hydroxylated, $C_6$-$C_{22}$ alkyl group, particularly preferably α-(2-ethylhexyl) glycerol ether, commercially available as Sensiva® SC 50 (ex Schülke & Mayr), carboxylic acid esters of monoglycerol, diglycerol and triglycerol (such as glycerol monolaurate, diglycerol monocaprinate), lantibiotics, and plant extracts (such as green tea and components of lime blossom oil) are preferred deodorizing active ingredients.

Further preferred deodorizing active ingredients are selected from what are known as prebiotically active components, which shall be understood to mean such components which inhibit solely, or at least predominantly, the odor-causing bacteria of the skin microflora, but not the desired, which is to say not odor-causing bacteria that are part of a healthy skin microflora. The active ingredients disclosed as being prebiotically active in unexamined patent applications DE 10333245 and DE 102004011968 shall be explicitly mentioned here; among these are coniferous tree extracts, in particular from the group of the Pinaceae, and plant extracts from the group of the Sapindaceae, Araliaceae, Lamiaceae and Saxifragaceae, in particular extracts of *Picea* spp., *Paullinia* sp., *Panax* sp., *Lamium album* or *Ribes nigrum*, and mixtures of these substances.

Further preferred deodorizing active ingredients are selected from the antimicrobially active perfume oils and the Deosafe perfume oils, which are available from Symrise, formerly Haarmann and Reimer.

Deodorizingly acting enzyme inhibitors are those substances that inhibit the enzymes responsible for the decomposition of sweat, in particular arylsulfatase, β-glucuronidase, aminoacylase, ester-cleaving lipases and lipoxigenase, wherein zinc glycinate is preferred.

The above-mentioned deodorizing active ingredient(s) can preferably be present in the aerosol compositions according to the invention in a total amount of 0.1 to 10 wt. %, more preferably of 0.2 to 7.5 wt. %, particularly preferably of 0.3-5 wt. %, and particularly preferably of 0.5 to 3.0 wt. %, based on the total weight of composition A.

Furthermore, preferred aerosol compositions according to the invention are characterized by comprising at least one encapsulated and/or at least one non-encapsulated fragrance.

The encapsulation of the fragrances can preferably be selected so as to comprise at least one water-soluble encapsulation material. Under the influence of moisture, which here is in particular under the influence of skin moisture or perspiration, the water-soluble encapsulation material opens a certain time after application, and the encapsulated fragrance and optionally further encapsulated active ingredients, such as skin-cooling active ingredients, are released with time delay after application.

Encapsulated and non-encapsulated fragrances, such as perfume oils or perfume oil mixtures, can be the same or different. Particularly preferred deodorizing aerosol compositions according to the invention are characterized by comprising at least one encapsulated and at least one non-encapsulated fragrance, which are different from one another.

Preferred deodorizing aerosol compositions according to the invention are characterized by comprising at least one non-encapsulated fragrance in a total amount of 0.1 to 3 wt. %, preferably 0.2 to 1.5 wt. %, and particularly preferably 0.4 to 1 wt. %, each based on the total weight of the aerosol composition.

Further preferred deodorizing aerosol compositions according to the invention are characterized by comprising at least one encapsulated fragrance in a total amount of 0.01 to 2 wt. %, preferably 0.1 to 1.0 wt. %, and particularly preferably 0.25 to 0.5 wt. %, each based on the total weight of the aerosol composition.

Odorant compounds, such as synthetic products of the ester, ether, aldehyde, ketone, alcohol, and hydrocarbon types, can be used particularly preferably as fragrances or perfume oils. Carvacrol, for example, is one of the preferred phenolic odorant compounds. Preferred odorant compounds of the ester type are, for example, benzyl acetate, methyl anthranilate, ortho-t-butylcyclohexyl acetate, p-tert.-butyl-cyclohexyl acetate, diethyl phthalate, nonanediol-1,3-diacetate, isononyl acetate, isononyl formiate, phenylethyl phenylacetate, phenoxyethyl isobutyrate, linalyl acetate, dimethyl benzyl carbinyl acetate, phenylethyl acetate, linalyl benzoate, benzyl formiate, ethyl methylphenylglycinate, allyl cyclohexyl propionate, styrallyl propionate, benzyl salicylate, ethyl salicylate, isoamyl salicylate, hexyl salicylate, and 4-nonanolide. The preferred ethers include, for example, benzyl ethyl ethers, the preferred aldehydes include, for example, linear alkanals having 8 to 18 carbon atoms, citral, citronellal, citronellyl oxy acetaldehyde, cyclamen aldehyde, hydroxycitronellal, lilial and bourgeonal, the preferred ketones include, for example, 6-acetyl-1,1,3,4,4,6-hexamethyltetrahydronaphthalene, para-t-amyl cyclohexanone, 2-n-heptyl cyclopentanone, β-methyl naphthyl ketone, and the ionones include α-isomethyl ionone and methyl cedryl ketone, the preferred alcohols include cinnamon alcohol, anethol, citronellol, dimyrcetol, eugenol, geraniol, linalool, phenylethyl alcohol and terpineol, the preferred hydrocarbons include 1,3,4,6,7,8-hexahydro-4,6,6,7,8,8-hexamethylcyclopenta-a-2-benzopyrane, hydroxymethyl isopropyl cyclopentane, 3a-methyldodecahydro-6,6,9a-trimethylnaphtho-2(2,1-b)furan, isobutyl quinoline, and the terpenes and balsams. Particularly preferably, mixtures of different odorants are used, which together produce an appealing odorous note.

Particularly preferred perfume oils can also include natural odorant mixtures such as those accessible from plant or animal sources, for example pine, citrus, jasmine, ylang, rose, or lily oil. Essential oils having lower volatility, which are usually used as aroma components, are particularly preferred as perfume oils, such as sage oil, chamomile oil, balm oil, mint oil, cinnamon leaf oil, lime blossom oil, juniper berry oil, vetiver oil, olibanum oil, galbanum oil, laudanum oil, clove oil, isoeugenol, thyme oil, rose oil, bergamot oil, and *geranium* oil.

Preferred capsule materials are water-soluble polymers, such as starch, physically and/or chemically modified starches, cellulose derivatives, such as carboxymethyl cellulose, methyl cellulose, hydroxyethyl cellulose or hydroxypropyl methyl cellulose, carrageenans, alginates, maltodextrins, dextrins, gums, pectins, xanthans, polyvinyl acetate and polyvinyl alcohol, polyvinylpyrrolidone, polyamides, polyesters, and homopolymers and copolymers of monomers, selected from acrylic acid, methacrylic acid, maleic acid, fumaric acid, itaconic acid, and the esters and the salts of these acids, and arbitrary mixtures of these polymers.

Particularly preferred capsule materials are chemically modified starches, and in particular aluminum starch octenylsuccinate, such as the commercial product Dry Flo Plus from National Starch, or sodium starch octenylsuccinate, such as the commercial product Tylose H 10 from Clariant, furthermore carboxymethyl cellulose, carboxymethyl cellulose, methyl cellulose, hydroxyethyl cellulose and hydroxypropyl methyl cellulose, furthermore carrageenans, alginates and maltodextrins, and arbitrary mixtures of these polymers.

Particularly preferred capsule materials are polymer mixtures composed of chemically modified starches and/or hydroxyethyl cellulose and a content of 0.2 to 2 wt. % of alginates and/or carrageenans.

The encapsulation can be carried out according to known methods. Appropriate methods are disclosed in K. Master, "Spray Drying Handbook", 3rd edition, John Wiley, 1979, for example. In a particularly preferred encapsulation method, a water-based mixture is prepared, comprising approximately 20 to 50 wt. % of the polymeric encapsulation material, approximately 0.1 to 2.0 wt. % of an emulsifier, approximately 5 to 20 wt. % of the perfume oil to be encapsulated and/or of the skin-cooling active ingredient to be encapsulated, and approximately 40 to 60 wt. % water. This mixture is homogenized and then spray-dried. The capsules loaded with the active ingredient are thus obtained as a fine powder having a particle diameter of 1 to 150 μm, preferably 20 to 80 μm, and particularly preferably 5 to 50 μm.

In another production process, the microencapsulation is carried out by way of coacervation, wherein gelatin is preferably used for the carrier.

The capsule material, composed of water-soluble polymers and a low content of emulsifiers, allows reversible "re-encapsulation" of the encapsulated perfume oils and skin-cooling active ingredients. The re-encapsulation occurs in situ during the drying process on the skin, which follows a perspiration period. In this way, different consecutive activations occur on the skin, without the user having to carry out another application of the agent according to the invention.

According to the invention, fragrance-free or perfume-free deodorizing aerosol compositions may also be preferred.

The aerosol compositions according to the invention are preferably packaged in commercially available aerosol cans. The cans can be made of tin plate or aluminum.

According to a particularly preferred embodiment, the cans may furthermore be coated on the inside so as to minimize the risk of corrosion to the extent possible.

The aerosol cans are preferably equipped with a suitable spray head. Depending on the spray head, ejection rates of 0.1 g/s to 2.0 g/s are preferred, based on full cans.

Compared to commercially available aerosol compositions, the aerosol compositions according to the invention have the advantage that they have an improved antiperspirant active ingredient delivery to the skin. In this way, the antiperspirant effectiveness of the aerosol can be enhanced.

A second subject matter of the invention is the cosmetic use of a mixture of propylene carbonate (iii) and at least one hydrophobized clay material (ii) at a weight ratio of (iii):(ii) of 1.75:1.00 to 2.00:1.00 in antiperspirant aerosol compositions for improving the delivery rate of the antiperspirant active ingredient(s) when sprayed onto the skin.

A third subject matter of the invention is the cosmetic non-therapeutic use of the aerosol composition according to the invention for reducing or masking body odor.

A fourth subject matter of the invention is a method for improving the antiperspirant effectiveness of aerosol compositions, in which a mixture of propylene carbonate (iii) and at least one hydrophobized clay material (ii) is added to a propellant-containing antiperspirant aerosol composition at a weight ratio of (iii):(ii) of 1.75:1.00 to 2.00:1.00.

A fifth subject matter of the invention is a cosmetic, non-therapeutic method for reducing or masking body odor, in which an aerosol composition according to the invention is sprayed onto the skin.

What was said above with respect to the compositions according to the invention applies, mutatis mutandis, to the use according to the invention and to the methods according to the invention.

The following examples are intended to illustrate the invention, without thereby limiting the invention to these examples.

Examples

I. Exemplary Embodiments

The following aerosol compositions according to the invention were produced. Unless indicated otherwise, all quantity information in the table below refers to wt. % in composition A.

| | Formula 1 | Formula 2 | Formula 3 | Formula 4 |
|---|---|---|---|---|
| Antiperspirant active ingredient | 5.0-60.0 | 10.0-50.0 | 15.0-40.0 | 20.0-35.0 |
| Hydrophobized clay material | 0.5-3.5 | 0.5-3.0 | 1.0-3.0 | 1.5-2.5 |
| Propylene carbonate | 1.0-7.0 | 1.5-6.0 | 2.0-5.0 | 2.5-4.0 |
| Carrier | to make up to 100 | to make up to 100 | to make up to 100 | to make up to 100 |

| | Formula 5 | Formula 6 | Formula 7 | Formula 8 |
|---|---|---|---|---|
| Aluminum chlorohydrate, aluminum sesquichlorohydrate and/or aluminum chloride | 5.0-60.0 | 10.0-50.0 | 15.0-40.0 | 20.0-35.0 |
| Hydrophobized clay material | 0.5-3.5 | 0.5-3.0 | 1.0-3.0 | 1.5-2.5 |
| Propylene carbonate | 1.0-7.0 | 1.5-6.0 | 2.0-5.0 | 2.5-4.0 |
| Carrier | to make up to 100 | to make up to 100 | to make up to 100 | to make up to 100 |

| | Formula 9 | Formula 10 | Formula 11 | Formula 12 |
|---|---|---|---|---|
| Antiperspirant active ingredient | 5.0-60.0 | 10.0-50.0 | 15.0-40.0 | 20.0-35.0 |

-continued

| | | | | |
|---|---|---|---|---|
| Montmorrillonites, hectorites and/or bentonites hydrophobically modified with mono- and/or di-$C_{10}$-$C_{24}$-alkyl-di-$C_1$-$C_4$-alkylammonium salts | 0.5-3.5 | 0.5-3.0 | 1.0-3.0 | 1.5-2.5 |
| Propylene carbonate Carrier | 1.0-7.0 to make up to 100 | 1.5-6.0 to make up to 100 | 2.0-5.0 to make up to 100 | 2.5-4.0 to make up to 100 |

| | Formula 13 | Formula 14 | Formula 15 | Formula 16 |
|---|---|---|---|---|
| Antiperspirant active ingredient | 5.0-60.0 | 10.0-50.0 | 15.0-40.0 | 20.0-35.0 |
| Disteardimonium Hectorite, Quaternium-18 Hectorite, Stearalkonium Bentonite and/or Quaternium-18 Bentonite | 0.5-3.5 | 0.5-3.0 | 1.0-3.0 | 1.5-2.5 |
| Propylene carbonate Carrier | 1.0-7.0 to make up to 100 | 1.5-6.0 to make up to 100 | 2.0-5.0 to make up to 100 | 2.5-4.0 to make up to 100 |

| | Formula 17 | Formula 18 | Formula 19 | Formula 20 |
|---|---|---|---|---|
| Antiperspirant active ingredient | 5.0-60.0 | 10.0-50.0 | 15.0-40.0 | 20.0-35.0 |
| Disteardimonium hectorite (Bentone® 38) | 0.5-3.5 | 0.5-3.0 | 1.0-3.0 | 1.5-2.5 |
| Propylene carbonate Carrier | 1.0-7.0 to make up to 100 | 1.5-6.0 to make up to 100 | 2.0-5.0 to make up to 100 | 2.5-4.0 to make up to 100 |

| | Formula 21 | Formula 22 | Formula 23 | Formula 24 |
|---|---|---|---|---|
| Aluminum chlorohydrate, aluminum sesquichlorohydrate and/or aluminum chloride | 5.0-60.0 | 10.0-50.0 | 15.0-40.0 | 20.0-35.0 |
| Montmorrillonites, hectorites and/or bentonites hydrophobically modified with mono- and/or di-$C_{10}$-$C_{24}$-alkyl-di-$C_1$-$C_4$-alkylammonium salts | 0.5-3.5 | 0.5-3.0 | 1.0-3.0 | 1.5-2.5 |
| Propylene carbonate Carrier | 1.0-7.0 to make up to 100 | 1.5-6.0 to make up to 100 | 2.0-5.0 to make up to 100 | 2.5-4.0 to make up to 100 |

| | Formula 25 | Formula 26 | Formula 27 | Formula 28 |
|---|---|---|---|---|
| Aluminum chlorohydrate, aluminum sesquichlorohydrate and/or aluminum chloride | 5.0-60.0 | 10.0-50.0 | 15.0-40.0 | 20.0-35.0 |
| Disteardimonium Hectorite, Quaternium-18 Hectorite, Stearalkonium Bentonite and/or Quaternium-18 Bentonite | 0.5-3.5 | 0.5-3.0 | 1.0-3.0 | 1.5-2.5 |
| Propylene carbonate Carrier | 1.0-7.0 to make up to 100 | 1.5-6.0 to make up to 100 | 2.0-5.0 to make up to 100 | 2.5-4.0 to make up to 100 |

| | Formula 29 | Formula 30 | Formula 31 | Formula 32 |
|---|---|---|---|---|
| Aluminum chlorohydrate (Reach® 103) | 5.0-60.0 | 10.0-50.0 | 15.0-40.0 | 20.0-35.0 |
| Disteardimonium hectorite (Bentone® 38) | 0.5-3.5 | 0.5-3.0 | 1.0-3.0 | 1.5-2.5 |
| Propylene carbonate Carrier | 1.0-7.0 to make up to 100 | 1.5-6.0 to make up to 100 | 2.0-5.0 to make up to 100 | 2.5-4.0 to make up to 100 |

| | Formula 33 | Formula 34 | Formula 35 | Formula 36 |
|---|---|---|---|---|
| Antiperspirant active ingredient | 5.0-60.0 | 10.0-50.0 | 15.0-40.0 | 20.0-35.0 |
| Hydrophobized clay material | 0.5-3.5 | 0.5-3.0 | 1.0-3.0 | 1.5-2.5 |
| Propylene carbonate | 1.0-7.0 | 1.5-6.0 | 2.0-5.0 | 2.5-4.0 |
| Silicone oil and/or ester oil | 30.0-85.0 | 35.0-80.0 | 40.0-75.0 | 45.0-70.0 |

| | Formula 37 | Formula 38 | Formula 39 | Formula 40 |
|---|---|---|---|---|
| Aluminum chlorohydrate, aluminum sesquichlorohydrate and/or aluminum chloride | 5.0-60.0 | 10.0-50.0 | 15.0-40.0 | 20.0-35.0 |
| Montmorrillonites, hectorites and/or bentonites hydrophobically modified with mono- and/or di-$C_{10}$-$C_{24}$-alkyl-di-$C_1$-$C_4$-alkylammonium salts | 0.5-3.5 | 0.5-3.0 | 1.0-3.0 | 1.5-2.5 |
| Propylene carbonate | 1.0-7.0 | 1.5-6.0 | 2.0-5.0 | 2.5-4.0 |
| Silicone oil and/or ester oil | 30.0-85.0 | 35.0-80.0 | 40.0-75.0 | 45.0-70.0 |

| | Formula 41 | Formula 42 | Formula 43 | Formula 44 |
|---|---|---|---|---|
| Aluminum chlorohydrate, aluminum sesquichlorohydrate and/or aluminum chloride | 5.0-60.0 | 10.0-50.0 | 15.0-40.0 | 20.0-35.0 |
| Disteardimonium Hectorite, Quaternium-18 Hectorite, Stearalkonium Bentonite and/or Quaternium-18 Bentonite | 0.5-3.5 | 0.5-3.0 | 1.0-3.0 | 1.5-2.5 |
| Propylene carbonate | 1.0-7.0 | 1.5-6.0 | 2.0-5.0 | 2.5-4.0 |
| Silicone oil and/or ester oil | 30.0-85.0 | 35.0-80.0 | 40.0-75.0 | 45.0-70.0 |

| | Formula 45 | Formula 46 | Formula 47 | Formula 48 |
|---|---|---|---|---|
| Aluminum chlorohydrate (Reach® 103) | 5.0-60.0 | 10.0-50.0 | 15.0-40.0 | 20.0-35.0 |
| Disteardimonium hectorite (Bentone® 38) | 0.5-3.5 | 0.5-3.0 | 1.0-3.0 | 1.5-2.5 |

-continued

| | Formula 45 | Formula 46 | Formula 47 | Formula 48 |
|---|---|---|---|---|
| Propylene carbonate | 1.0-7.0 | 1.5-6.0 | 2.0-5.0 | 2.5-4.0 |
| Silicone oil and/or ester oil | 30.0-85.0 | 35.0-80.0 | 40.0-75.0 | 45.0-70.0 |

| | Formula 49 | Formula 50 | Formula 51 | Formula 52 |
|---|---|---|---|---|
| Aluminum chlorohydrate (Reach® 103) | 5.0-60.0 | 10.0-50.0 | 15.0-40.0 | 20.0-35.0 |
| Disteardimonium hectorite (Bentone® 38) | 0.5-3.5 | 0.5-3.0 | 1.0-3.0 | 1.5-2.5 |
| Propylene carbonate | 1.0-7.0 | 1.5-6.0 | 2.0-5.0 | 2.5-4.0 |
| Cyclopentasiloxane | 20.0-70.0 | 25.0-65.0 | 30.0-60.0 | 35.0-50.0 |
| Ethylhexyl palmitate | 2.0-20.0 | 3.0-18.0 | 4.0-15.0 | 6.0-10.0 |
| Triethyl citrate | 0.1-10.0 | 0.2-7.0 | 0.3-5.0 | 0.5-2.0 |
| Perfume | 1.0-10.0 | 2.0-9.0 | 3.0-8.0 | 4.0-8.0 |

10.0 to 40 wt. %, preferably 15.0 to 40.0 wt. %, particularly preferably 20.0 to 35.0 wt. %, and in particular 25.0 to 30.0 wt. % of compositions A from the above tables can be filled into commercially available aerosol cans at a weight ratio (1:4), for example with the propellant propane/butane (15/85), and sprayed.

The weight ratio of propylene carbonate (iii) to the hydrophobized clay material (ii) is selected within the above-described limits such that it is in the range from 1.75:1.00 to 2.00:1.00.

II. Proof of Effectiveness

Antiperspirant suspensions were produced, having the following compositions (the quantity information refers to wt. %):

| | E1 | E2 | V1 | V2 | V3 | V4 | V5 | V6 | V7 |
|---|---|---|---|---|---|---|---|---|---|
| A: Cyclopentasiloxane | 40.5 | 40.0 | 41.6 | 43.1 | 42.5 | 42.0 | 41.5 | 41.0 | 39.5 |
| A: Ethylhexyl palmitate | 7.0 | 7.0 | 7.0 | 7.0 | 7.0 | 7.0 | 7.0 | 7.0 | 7.0 |
| A: Isopropyl myristate | 6.0 | 6.0 | 6.0 | 6.0 | 6.0 | 6.0 | 6.0 | 6.0 | 6.0 |
| A: Triethyl citrate | 1.0 | 1.0 | 1.0 | 1.0 | 1.0 | 1.0 | 1.0 | 1.0 | 1.0 |
| Perfume | 6.7 | 6.7 | 6.7 | 6.7 | 6.7 | 6.7 | 6.7 | 6.7 | 6.7 |
| (i): Aluminum chlorohydrate (Reach® 103) | 33.3 | 33.3 | 33.3 | 33.3 | 33.3 | 33.3 | 33.3 | 33.3 | 33.3 |
| (ii): Disteardimonium hectorite (Bentone® 38 V CG) | 2.0 | 2.0 | 2.5 | 2.0 | 2.0 | 2.0 | 2.0 | 2.0 | 2.0 |
| (iii): Propylene carbonate | 3.5 | 4.0 | 0.9 | 0.9 | 1.5 | 2.0 | 2.5 | 3.0 | 4.5 |
| (iii):(ii) | 1.75 | 2.00 | 0.36 | 0.45 | 0.75 | 1.00 | 1.25 | 1.50 | 2.25 |
| Spray rate [g/2 sec] | 0.31 | 0.33 | 0.30 | 0.31 | 0.32 | 0.29 | 0.30 | 0.32 | 0.33 |
| Viscosity [mPas] | 5250 | 5700 | 3000 | 2800 | 3600 | 4600 | 5000 | 4950 | 6200 |
| Delivered amount of aluminum chlorohydrate [mg] | 7.5 | 7.3 | 6.0 | 6.6 | 6.5 | 6.3 | 6.3 | 6.4 | 6.5 |

So as to produce the antiperspirant suspensions, components A were heated to 30° C. in a water bath, and subsequently Bentone® 38 V CG was slowly added while stirring. The batch was allowed to swell in the water bath for 15 minutes. Thereafter, it was homogenized for 20 seconds, and subsequently aluminum chlorohydrate was added while stirring. After the batch was homogenized for another 20 minutes, the respective amounts of propylene carbonate were slowly added while stirring, and the batch was homogenized for another 10 seconds.

Finally, the perfume oil was added.

Formulations E1 to V7 were each filled into aerosol cans at a weight ratio of 1:4 to the propellant propane/butane (15/85).

Each aerosol E1 to V7 was sprayed for 2 seconds onto a beaker glass. Thereafter, the delivered product was eluted, and the content of chloride ions in the eluate was ascertained by way of potentiometry. Via the known chloride-to-aluminum ratio of the aluminum chlorohydrate (Reach® 103) used, it is possible to calculate the aluminum content.

The above-mentioned table in item II. of the exemplary section shows that optimal active ingredient delivery is achieved with formulations E1 and E2 according to the invention.

If the weight ratio of the propylene carbonate (iii) to the hydrophobized clay material (ii) in the formulations is outside the range of 1.75:1.00 to 2.00:1.00 (formulations V1 to V6: below; formulation V7: above the range), a considerably lower antiperspirant active ingredient delivery can be observed for the same spray rate of the respective aerosol.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An aerosol composition for body care, comprising:
   a) at least one propellant, and
   b) a composition A, including,
      (i) at least one perspiration-inhibiting antiperspirant active ingredient, (ii) at least one hydrophobized clay material, and
(iii) propylene carbonate
wherein the weight ratio of propylene carbonate (iii) to the hydrophobized clay material (ii) is 1.75:1.00 to 2.00:1.00.

2. The aerosol composition according to claim 1, wherein composition A is anhydrous.

3. The aerosol composition according to claim 1, wherein the hydrophobized clay material (ii) is selected from the group consisting of: montmorrillonites, hectorites and/or bentonites, which were hydrophobically modified with cationic surfactants.

4. The aerosol composition according to claim 1, wherein the hydrophobized claim material (ii) is hydrophobically modified with mono- and/or di-$C_{10}$-$C_{24}$-alkyl-di-$C_1$-$C_4$-alkylammonium salts.

5. The aerosol composition according to claim 1, wherein the hydrophobized clay material (ii) is selected from the group consisting of: distearyldimethylammonium hectorite (INCI: Disteardimonium Hectorite), compounds known under the INCI names Quaternium-18 Hectorite, Stearalkonium Bentonite, and/or Quaternium-18 Bentonite.

6. The aerosol composition according to claim 1, wherein the percentage by weight of the hydrophobized clay material (ii) relative to the total weight of composition A), is 0.5 to 3.5 wt. %.

7. The aerosol composition according to claim 1, wherein the percentage by weight of the hydrophobized clay material (ii) relative to the total weight of composition A), is 1.0 to 3.0 wt. %.

8. The aerosol composition according to claim 1, wherein the percentage by weight of the hydrophobized clay material (ii) relative to the total weight of composition A), is 1.5 to 2.5 wt. %.

9. The aerosol composition according to claim 1, wherein the percentage by weight of propylene carbonate relative to the total weight of composition A is 1.0 to 7.0 wt. %.

10. The aerosol composition according to claim 1, wherein the percentage by weight of propylene carbonate relative to the total weight of composition A is 2.0 to 5.0%.

11. The aerosol composition according to claim 1, wherein the percentage by weight of propylene carbonate relative to the total weight of composition A is 2.5 to 4.0 wt. %.

12. The aerosol composition according to claim 1, wherein the at least one antiperspirant active ingredient (i) is an astringent aluminum salts and the total weight of composition A of 5 to 60 wt. % based on the total relative weight of the aerosol composition.

13. The aerosol composition according to claim 1, wherein the at least one antiperspirant active ingredient (i) is an astringent aluminum salts and the total weight of composition A of 15 to 40 wt. % based on the total relative weight of the aerosol composition.

14. The aerosol composition according to claim 1, wherein the at least one antiperspirant active ingredient (i) is aluminum chlorohydrate, aluminum sesquichlorohydrate and/or aluminum chloride.

15. The aerosol composition according to claim 1, wherein composition A comprises at least one oil that is liquid at 25 C and 1 ATM, wherein the percentage by weight of the liquid oil relative to the total weight of composition A is 30 to 85 wt. %.

16. The aerosol composition according to claim 15, wherein composition A comprises at least one oil that is liquid at 25 C and 1 ATM, wherein the percentage by weight of the liquid oil relative to the total weight of composition A is 45 to 70 wt. %.

17. The aerosol composition according to claim 15, wherein the at least one oil that is liquid at 25 C and 1 ATM includes at least one ester oil and/or at least one silicone oil.

18. The aerosol composition according to claim 15, wherein the oil that is liquid at 25 C and 1 ATM is a mixture of
triethyl citrate in a percentage by weight of 0.1 to 10.0 wt. % relative to the total weight of composition A;
at least one volatile silicone oil in a percentage by weight of 20.0 to 70.0 wt. %, relative to the total weight of composition A; and
at least one $C_{10}$-$C_{24}$ carboxylic acid ester, relative to the total weight of composition A.

19. The aerosol composition according to claim 1, wherein the propellant a) is selected from the group consisting of: propane, n-butane, isobutane, n-pentane, isopentane and the mixtures thereof.

20. The aerosol composition according to claim 1, wherein
the percentage by weight of propellant a) relative to the total weight of the aerosol composition is 10 to 90 wt. %, and
the percentage by weight of compositions A relative to the total weight of the aerosol composition is 1 to 40 wt. %.

* * * * *